United States Patent [19]

Tsutomu et al.

[11] Patent Number: 5,744,608
[45] Date of Patent: Apr. 28, 1998

[54] METHOD FOR MANUFACTURING 3-(AMINOMETHYL)-6-CHLOROPYRIDINES

[75] Inventors: Inoue Tsutomu, Odawara; Takahashi Jun; Imagawa Tsutomu, both of Takaoka; Kazuhiro Hatanaka, Himi, all of Japan

[73] Assignee: Nippon Soda Co., Ltd., Tokyo, Japan

[21] Appl. No.: 836,658

[22] PCT Filed: Sep. 6, 1996

[86] PCT No.: PCT/JP96/02535

§ 371 Date: May 1, 1997

§ 102(e) Date: May 1, 1997

[87] PCT Pub. No.: WO97/09312

PCT Pub. Date: Mar. 13, 1997

[30] Foreign Application Priority Data

Sep. 8, 1995 [JP] Japan ................ 7-257116
Nov. 15, 1995 [JP] Japan ................ 7-321111

[51] Int. Cl.$^6$ ................ C07D 213/38; C07D 213/26
[52] U.S. Cl. ................ 546/329
[58] Field of Search ................ 546/329; 504/244

[56] References Cited

U.S. PATENT DOCUMENTS

| | | | |
|---|---|---|---|
| 4,576,629 | 3/1986 | Garst et al. | 504/217 |
| 5,026,864 | 6/1991 | Diehr | 546/345 |
| 5,300,650 | 4/1994 | Nabata | 546/329 |
| 5,382,671 | 1/1995 | Diehr | 546/329 |
| 5,424,437 | 6/1995 | Ieno | 546/329 |
| 5,502,194 | 3/1996 | Rivadeneira | 546/257 |
| 5,580,983 | 12/1996 | Kraus | 546/336 |

FOREIGN PATENT DOCUMENTS

| | | |
|---|---|---|
| 256990 A | 2/1988 | European Pat. Off. |
| 302389 A | 2/1989 | European Pat. Off. |
| 366085 A | 5/1990 | European Pat. Off. |
| 376279 A | 7/1990 | European Pat. Off. |
| 391205 A | 10/1990 | European Pat. Off. |
| 425030 A | 5/1991 | European Pat. Off. |
| 512463 A1 | 11/1992 | European Pat. Off. |
| 556683 A1 | 8/1993 | European Pat. Off. |
| 569974 A2 | 11/1993 | European Pat. Off. |
| 3630046 A | 3/1988 | Germany |
| 4016175 A | 11/1991 | Germany |
| 4222152 A1 | 1/1994 | Germany |
| 2-290851 | 11/1990 | Japan |
| 5-286936 | 11/1993 | Japan |
| 05320132 A | 12/1993 | Japan |
| 6-279410 | 10/1994 | Japan |
| 7-188170 | 7/1995 | Japan |
| 8-27112 | 1/1996 | Japan |
| 8-53417 | 2/1996 | Japan |
| WO9213840 A1 | 8/1992 | WIPO |

*Primary Examiner*—C. Warren Ivy
*Assistant Examiner*—D. Margaret M. Mach
*Attorney, Agent, or Firm*—Joseph C. Mason, Jr.

[57] ABSTRACT

The present invention is directed to methods for manufacturing 3-(aminomethyl)-6-chloropyridines represented by a general formula [II];

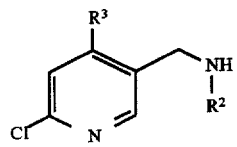

wherein $R^2$ represents hydrogen or a lower alkyl and $R^3$ represents hydrogen, a lower alkyl or an halogen atom, characterized in that the compound represented by the general formula [II] is manufactured by allowing 3-(substituted-aminomethyl)pyridine 1-oxide represented by a general formula [I];

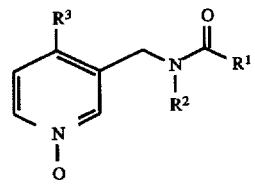

wherein $R^1$ represents alkyl, aryl, aralkyl or alkoxy, $R^2$ and $R^3$ are as described above, to react with a base represented by a general formula [a];

R'R"R'''N  [a]

wherein R', R" and R''' may be the same or different one another and represent each independently a lower alkyl or an aromatic group, or R', R", R''' and N may form together an optionally-substituted pyridine ring, in the presence of an electrophilic reagent having at least one chlorine atom, and subsequently treating the reaction product with hydrogen chloride and water.

The compounds manufactured according to the present invention are useful as the raw materials used for the manufacturing of agricultural chemicals and pharmaceuticals, and particularly useful for the raw materials for manufacturing insecticides.

10 Claims, No Drawings

METHOD FOR MANUFACTURING 3-(AMINOMETHYL)-6-CHLOROPYRIDINES

This application is a 371 of PCT/JP96/02535, filed Sep. 6, 1996.

FIELD OF THE INVENTION

The present invention relates to substituted-aminomethyl pyridines which are useful as a precursor for manufacturing important raw materials used for the production of plant protection chemicals.

BACKGROUND ART

Since 3-(aminomethyl)-6-chloropyridines represented by a general formula [II];

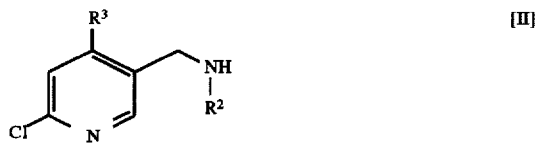

wherein $R^2$ is hydrogen or a lower alkyl, $R^3$ is hydrogen, a lower alkyl or a halogen atom, are known as an important raw material for manufacturing insecticides for agricultural use, many investigations have been made on the methods for the manufacturing said chloropyridines.

For instance, (1) a method to use 6-chloro-3-(chloromethyl)pyridine as a starting material and to convert the chlorine atom substituted on the methyl group therein to an amino group, which method is disclosed in EP 391205, EP 302389, EP 366085, EP 376279, and JP 5286936, and (2) a method to use 6-chloro-3-cyanopyridine as a precursor and to convert the cyano group therein to an aminomethyl group, which method is disclosed in DE 4222152 and WO 9213840, are known as such methods as described above.

However, the method (1) to convert the chlorine atom on the methyl group to an amino group as described above produces some by-products, such as the dimer thereof, and therefore, no satisfactory method to be employed in an industrial scale has been reported up till now. Furthermore, as a method for producing a raw material, 6-chloro-3-(chloromethyl)pyridine, the following methods, (i) chlorination of 6-chloro-3-methylpyridine, which is prepared pursuant to a method described in EP 556683, etc. (see DE 3630046 and DE 4016175), (ii) reduction of 6-chloro-3-(trichloromethyl)pyridine (see EP 512463 and JP 5320132) and (iii) preparation from 6-chloronicotinic acid (see EP 569974, EP 256990, U.S. Pat. No. 4576629 and BP 425030), are typically known. However, in case of the methods (i) and (ii), there is a problem in selectivity of the reaction, namely, it is difficult to allow only the objective first substitution reaction of the chlorine atom on the methyl group and then to stop the subsequent substitution reaction that follows, and the method (iii) has some problems in the cost and so on, since raw materials to be used for the method are expensive and the method requires a higher cost in the reduction process.

In the case of the method(2), it is also problem that elimination of a chlorine atom, the secondary production of dimers, etc. are caused during the reduction procedure of 6-chloro-3-cyanopyridine, and that 6-chloro-3-cyanopyridine can not be efficiently obtained due to the generation of its regioisomers at a time of chlorination of the 6th position of 3-cyanopyridine in the manufacturing process of the raw material.

Therefore, all of the methods previously known have faults that produce many by-products due to any reason of the elimination and the substitution of the chlorine atom, hydrogenation of the pyridine ring, production of the dimer, and so on, since all of the methods publicly-known take a reaction to establish an amino group on the 3rd-positioned methyl group following to the completion of chlorination at the 6th-position.

DISCLOSURE OF THE INVENTION

The inventors of the present invention, have seriously investigated to find an industrially-advantageous method for manufacturing 3-(aminomethyl)-6-chloropyridines represented by a general formula [II];

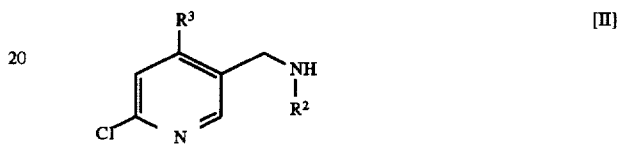

wherein $R^2$ and $R^3$ are as described above, and they have found that 3-(aminomethyl)-6-chloropyridines represented by a general formula [II];

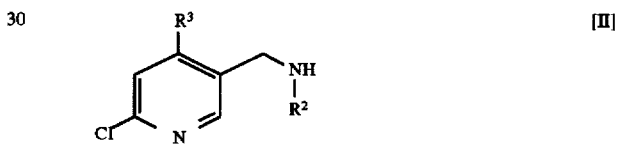

wherein $R^2$ and $R^3$ are as described above, can be efficiently manufactured by using 3-(substituted-aminomethyl) pyridine 1-oxide represented by a general formula [I];

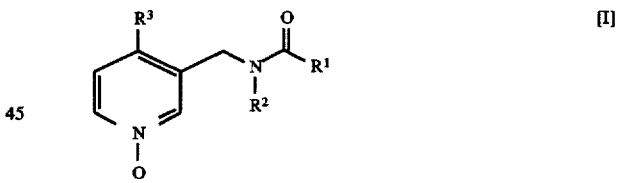

wherein $R^1$ is alkyl, aryl, aralkyl or alkoxy, $R^2$ and $R^3$ are as described above, as a starting raw material and have accomplished the present invention.

Therefore, the present invention is directed to methods for manufacturing 3-(aminomethyl)-6-chloropyridines represented by a general formula [II];

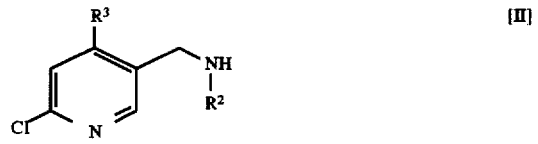

wherein $R^2$ and $R^3$ are as described above, characterized in that the said 3-(aminomethyl)-6-chloropyridines can be manufactured by allowing 3-(substituted-aminomethyl) pyridine 1-oxide represented by a general formula [I];

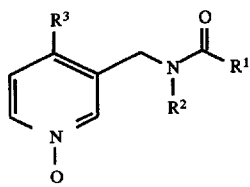

wherein $R^1$ represents alkyl, aryl, aralkyl or alkoxy, $R^2$ represents hydrogen or a lower alkyl, and $R^3$ represents a lower alkyl or an halogen atom, to react with a base represented by a general formula [a];

R'R"R'"N  [a]

wherein R', R" and R'" may be the same or different from one another and they are each independently a lower alkyl or an aromatic group, or R', R" , R'" and N may form together an optionally-substituted pyridine, in the presence of an electrophilic reagent having at least one chlorine atom, and subsequently treating the reaction product with hydrogen chloride and water.

Now, $R^1$, $R^2$ and $R^3$ are described more specifically hereinbelow.

For $R^1$, any one which can be stable under the both conditions of the oxidation for the preparation of a raw material compound represented by a general formula[I] and the formation of the quaterly ammornium salts at the 6-th position of the pyridine ring and is allowable to hydrolysis of an acylamino group in the presence of an acid in the water-treating process specified in the present invention as described above. As concrete examples thereof, alkyl, such as lineas, branched or cyclic $C_{1-18}$ alkyl, and aryl, such as phenyl or an aromatic groups in a form of a fused ring compounds including naphthalene, anthracene and the like, can be given, and further, such alkyl and aryl groups whereto a lower alkyl, such as methyl and ethyl, a lower alkoxy, such as methoxy and ethoxy, or an halogen atom, such as fluorine and chlorine, are substituted can be used as well. As the aralkyl groups described above, a combination made of the aforementioned alkyl and aryl groups can be used, and as the alkoxy group, a lower alkoxy including methoxy, ethoxy, isopropoxy, etc. and benzyloxy can be given for the examples. $R^2$ is hydrogen or a lower alkyl, such as methyl and ethyl, and $R^3$ is hydrogen, a lower alkyl, such as methyl and ethyl, or a halogen atom.

As examples of the base represented by the general formula [a], a trialkylamines, such as trimethylamine and triethylamine, a tertiary amine, such as N,N-dimethylaniline and N,N-dimethyl-4-aminopyridine, and a pyridine optionary subustituted with a lower alkyl, such as methyl and ethyl, and the like can be given.

As examples of the electrophilic reagent, chlorides, such as phosgene, thionyl chloride and sulfury chloride, phosphorus chlorides, such as phosphorus oxychloride, phosphorus pentachloride and (diethylamide)phosphonyl chloride, sulfonyl chlorides, such as methanesulfonyl chloride and toluenesulfonyl chloride, acid chlorides, such as acetyl chloride and benzoyl chloride, and chloroformates, such as methyl chloroformate and isopropyl chloroformate, can be given.

The method specified in the present invention can be expressed by the following reaction formula.

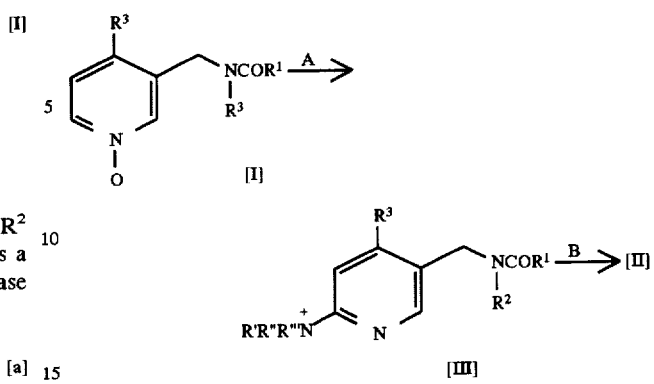

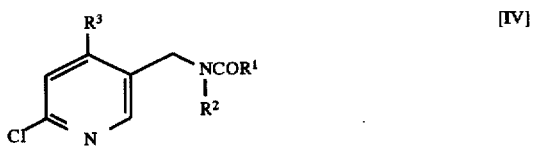

Process A

An electrophilic reagent is allowed to react with a compound represented by a general formula [I] and a base represented by a general formula [a] in a mixed solution to produce an ammonium salt represented by a general formula [III], wherein $R^1$, $R^2$, $R^3$, R', R" and R'" are as described above.

Process B

The ammonium salt [III] obtained in the Process A described above was allowed to react with hydrogen chloride in a nonaqueous inactive solvent to obtain 3-(acylaminomethyl)-6-chloropyridine represented by a general formula [IV];

[IV]

wherein $R^1$, $R^2$ and $R^3$ are as described above. 3-(acylaminomethyl)-6-chloropyridine obtained as described above was then allowed to hydrolysis in an aqueous solvent in the presence of an acid, such as hydrochloric acid, to obtain 3-(aminomethyl)-6-chloropyridines represented by a general formula [II]. Alternatively, by treating the ammonium salt represented by a general formula [III] in an aqueous solution of hydrogen chloride, a compound represented by the general formula [II] can be obtained directly.

As a solvent to be used in the Process A, any of inactive chlorine-containing solvents, such as methylene chloride, chloroform, carbon tetrachloride and chlorobenzene, inactive nitrile-type solvents, such as acetonitrile and benzonitrile, inactive ester-type solvents, such as ethyl acetate and methyl acetate, inactive ether-type solvents, such as THF and diethyl ether, inactive ketone-type solvents, such as acetone, MEK and mixtures thereof, and mixtures of any of the inactive solvent described above whereto a hydrocarbon-type solvent, such as hexane and toluene, is added, can be given as the examples. In the Process A, the base represented by a general formula [a] in an amount of from 2 to 6 mol based on the compound represented by the general formula [I] is used, whereas the electrophilic reagent in an amount of from 1 to 5 mol based on the compound represented by the general formula [I] is used. The reaction is proceeded for a period of from 1 to 6 hours at a temperature ranging from –40° C. to a boiling point of a solvent used, and more preferably from –20° C. to a room temperature.

As the nonaqueous solvent to be used for the treatment with hydrogen chloride in the Process B, the same solvents as used in the Process A can be given as the example, whereas as the aqueous solvent to be used for said hydrolysis, water or any of mixed-solvents consisting of water and a lower alcohol, such as methanol and ethanol, can be given as the example.

In order to directly obtain a compound represented by a general formula [II] from a compound represented by a general formula [III], the compound represented by a general formula [III] is allowed to react with hydrogen chloride in an amount of from 5 to 20 equivalents based on the compound represented by a general formula [III] for 3 to 20 hours in an aqueous solvent, which can be selected from the ones as described above, under a pressure ranging from an ordinary pressure to 10 kgf/cm$^2$, and more preferably from an ordinary pressure to 3 kgf/cm$^2$, and at a temperature of from 80° to 100° C. to obtain a compound represented by a general formula [II].

When using both nonaqueous and aqueous solvent in series, a compound represented by a general formula [IV] is firstly obtained by allowing a compound represented by a general formula [III] to react with hydrogen chloride in an amount of from 5 to 10 equivalents in a nonaqueous solvent under a pressure of from an ordinary pressure to 20 kgf/cm$^2$, and more preferably from an ordinary pressure to 10 kgf/cm$^2$, then the compound represented by a general formula [IV] is further allowed to react with hydrogen chloride in an amount of from 5 to 20 equivalents for 3 to 12 hours in an aqueous solvent at a temperature of from 60° C. to a boiling point of the solvent used, and more preferably from 85° to 95° C. to obtain a compound represented by a general formula [II].

For example, a raw material, 3-(substituted-aminomethyl) pyridine 1-oxide represented by a general formula [I] is manufactured from any of 3-(aminomethyl)pyridines represented by a general formula [V] pursuant to the following reaction formula.

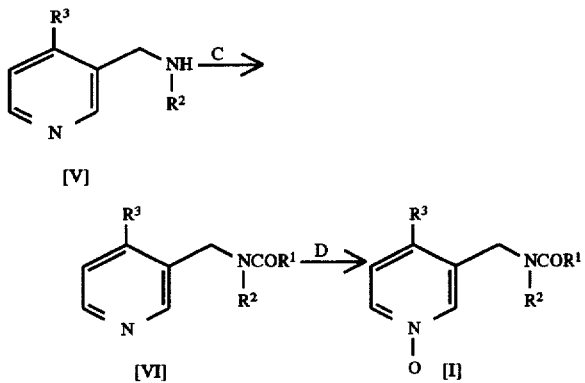

Process C proceeds in accordance with the process as described hereinbelow.

(1) When using any of acid halides, haloformates and acid anhydrides represented by a general formula, R$^1$COX [VII], wherein R$^1$ is as described above and X represents an halogen atom, or a general formula, (R$^1$CO)$_2$O [VIII], wherein R$^1$ is as described above:

A compound represented by a general formula [V] in an amount of 1 mol and a compound represented by a general formula either [VII] or [VIII] in an amount of 1 to 1.1 mol are allowed to react in an organic solvent, such as methylene chloride, chloroform, toluene and xylene, in the presence of an organic base, such as triethylamine, in an amount of 1 to 1.5 mol at a temperature of from −10° to 40° C.

Alternatively, the Process C can be achieved by using an inorganic base, such as sodium hydroxide in place of the organic base described above and subsequently proceeding a two-phase reaction at a temperature of from a room temperature to 50° C., and in the presence of a phase transfer catalyst, such as quaterly ammonium salts, if appropriate.

(2) When using any of esters represented by a general formula, R$^{1'}$COOY [IX], wherein R$^{1'}$ is alkyl, aryl or aralkyl and Y represents a lower alkyl:

A compound represented by a general formula [V] in an amount of 1 mol and an ester compound represented by a general formula [IX] in an amount of from 1.5 to 5.0 mol are allowed to a reaction in a solvent same as the one used in (1) described hereinabove at a temperature of from a room temperature to a boiling point of the solvent used in the presence of an acid catalyst, such as hydrogen chloride and sulfuric acid.

Process D is to obtain 3-(substituted-aminomethyl) pyridine 1-oxide represented by a general formula [I] shown hereinabove after oxidizing a compound represented by a general formula [VI] and is proceeded by using any of lower alcohols, water and acetic acid as a solvent and any of hydrogen peroxide, peracetic acid, metachloroperbenzoic acid, etc. in an amount of 1 to 2 equivalents as an oxidizing agent at a temperature of from a room temperature to a boiling point of the solvent used. In this reaction, it is also preferable to use a tungstate compound as a catalyst for obtaining a better result.

The compounds represented by a general formula [I] obtained as described above can be also used without carrying out their isolation as a raw material useful for the subsequent manufacturing process specified in the present invention.

BEST MODE FOR CARRYING OUT THE INVENTION

Now, the present invention is further described in detail with referring Examples and Referential Examples described hereinbelow.

EXAMPLE 1

Manufacturing of 3-(aminomethyl)-6-chloropyridine starting from 3-(benzamidomethyl)pyridine 1-oxide:

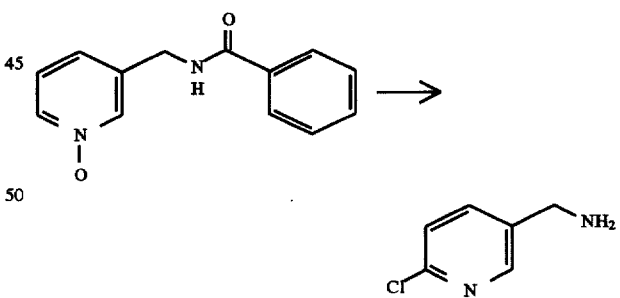

To 100 ml chloroform solution containing 3-(benzamidomethyl) pyridine 1-oxide in an amount of 6.9 g (0.03 mol) and trimethylamine in an amount of 6 g (0.10 mol), was added phosgene in an amount of 7 g (0.07 mol) at −5 ° C. while stirring and spending 1 hour. The reaction mixture was then heated up to a room temperature and was kept in stirring for 2 hours, and the mixture was then concentrated and dried at 40 ° C. under a pressure of 450 torr. The dried-product was further added with concentrated hydrochloric acid in a volume of 120 ml to allow them to a reaction for 15 hours at a temperature of from 80° to 100° C. After cooling the reaction mixture to a room temperature, the reaction mixture was then extracted with chloroform to recover benzoic acid resulted therein to an extent of 95%. By means of HPLC analysis, 3-(aminomethyl)-6-chloropyridine in an amount of 3.2 g was determined in the aqueous layer. The yield was 75%.

EXAMPLE 2

Manufacturing of 3-(aminomethyl)-6-chloropyridine starting from 3-(heptaneamidomethyl)pyridine 1-oxide:

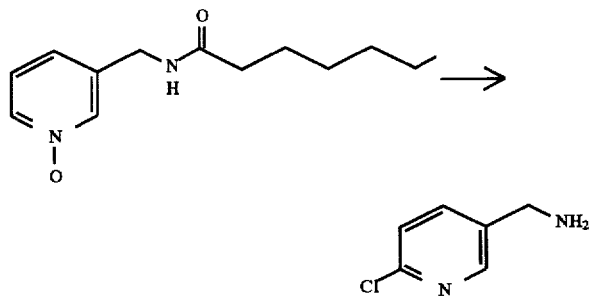

To 100 ml chloroform solution containing 3-(heptaneamidomethyl) pyridine 1-oxide in an amount of 10.4 g (0.05 mol) and trimethylamine in an amount of 8 g (0.13 mol), was added phosgene in an amount of 9 g (0.09 mol) at −5° C. while stirring and spending 1 hour. The reaction mixture was then heated up to a room temperature and was kept in stirring for 2 hours, and the mixture was then concentrated and dried at 40° C. under a pressure of 450 torr. The dried-product was further added with concentrated hydrochloric acid in a volume of 150 ml to allow them to a reaction for 3 hours at a temperature of from 60° to 70° C. and further subsequently for 5 hours at a temperature of from 90° to 100° C. After cooling the reaction mixture to a room temperature, the mixture was then extracted with chloroform to recover heptanoic acid resulted therein to an extent of 97%. The aqueous layer adjusted to pH 14.0 was repeatedly extracted with chloroform. By means of HPLC analysis, 3-(aminomethyl)-6-chloropyridine in an amount of 5.8 g was determined in the chloroform layer. The yield was 81%.

EXAMPLE 3

Manufacturing of 3-(aminomethyl)-6-chloropyridine starting from 3-(pivaloylaminomethyl)pyridine 1-oxide:

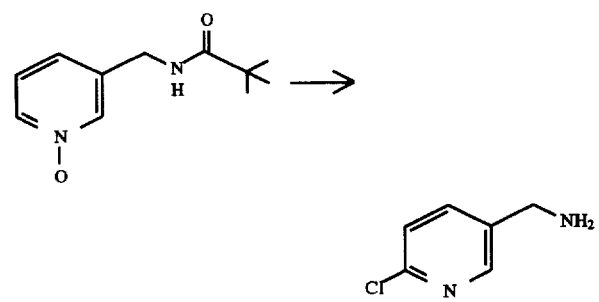

To 110 ml chloroform solution of 3-(pivaloylaminomethyl)pyridine 1-oxide in an amount of 20.8 g (0.1 mol), was added trimethylamine in an amount of 15.9 g (0.27 mol), and the reaction mixture was then added phosgene in an amount of 13.4 g (0.135 mol) at −5° C. while stirring and spending 30 minutes. The reaction mixture was further kept in stirring for 2 hours and was then concentrated and dried under reduced pressure. The dried-product was then added with 9-N hydrochloric acid in a volume of 300 ml and then heated for 12 hours at a temperature of from 90° to 95° C. After cooling the reaction mixture to a room temperature, the mixture was then extracted with chloroform to recover pivalic acid resulted therein to an extent of 78% and was added with 50% aqueous solution of sodium hydroxide to adjust the pH of the solution to 13.5. The solution was then extacted with 100 ml chloroform and the aqueous layer was further repeatedly extracted with chloroform. All chloroform layers were collected together to dry it with magnesium sulfate. By means of HPLC analysis, 3-(aminomethyl)-6-chloropyridine in an amount of 10.3 g (0.072 mole) was determined in the solution. The yield was 72%.

EXAMPLE 4

Manufacturing of 3-(aminomethyl)-6-chloropyridine starting from 3-(pivaloylaminomethyl)pyridine 1-oxide:

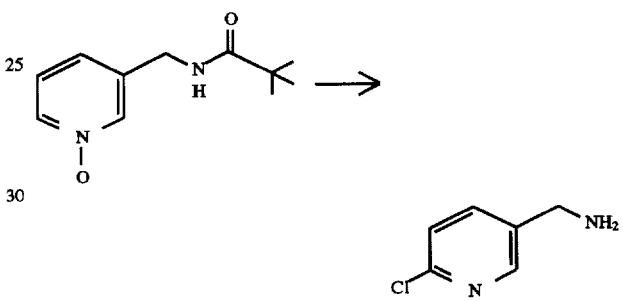

To 110 ml chloroform solution of 3-(pivaloylaminomethyl)pyridine 1-oxide in an amount of 20.8 g (0.1 mol), was added trimethylamine in an amount of 15.9 g (0.27 mol), and the reaction mixture was then phosgene in an amount of 13.4 g (0.135 mol) at −5° C. while stirring and spending 30 minutes. The reaction mixture was then transferred into an autoclave whereto hydrogen chloride gas in an amount of 40.2 g (1.1 mole) was subsequently introduced, then the solution was allowed to react for 5 hours at 60° C. under a pressure of 5 kgf/cm² while stirring. After cooling the reaction mixture to a room temperature, the solution was then extracted with 9-N hydrochloric acid in a volume of 300 ml. The hydrochloric acid solution obtained was then heated for 9 hours at a temperature of from 90° to 95° C. After cooling it to a room temperature, the reaction mixture was added with 50% aqueous solution of sodium hydroxide to adjust the pH of the solution to 13.5. The solution was then extracted with 100 ml chloroform and the aqueous layer was further repeatedly extracted with chloroform. All chloroform layers were collected together to dry it with magnesium sulfate and the solvent therein was removed by distillation, thereby affording 3-(aminomethyl) -6-chloropyridine in an amount of 12.0 g (0.084 mol) in a crystalline form. The yield was 84%.

EXAMPLE 5

Manufacturing of 3-(aminomethyl)-6-chloropyridine starting from 3-(isopropoxycarbonylaminomethyl)pyridine 1-oxide:

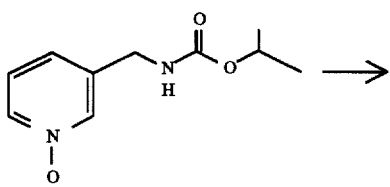

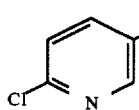

To 250 ml chloroform solution of 3-(isopropoxycarbonylaminomethyl) pyridine 1-oxide in an amount of 42.0 g (0.2 mol), was added trimethylamine in an amount of 29.6 g (0.5 mol), and the reaction mixture was then added phosgene in an amount of 24.0 g (0.24 mol) at −5° C. while stirring and spending 1 hour. The reaction mixture was then concentrated and dried under reduced pressure, then added with 35% hydrochloric acid in a volume of 160 ml and heated for 8 hours at a temperature of from 90° to 95° C. After cooling the reaction mixture to a room temperature, the mixture was then added with 28% aqueous solution of sodium hydroxide in a volume of 220 ml to adjust the pH of the solution to 13.5. The solution was then extracted with 150 ml chloroform and the aqueous layer was further repeatedly extracted with chloroform. All chloroform layers were collected together to dry it with magnesium sulfate. By means of HPLC analysis, 3-(aminomethyl)-6-chloropyridine in an amount of 21.3 g (0.15 mol) was determined in the solution. The yield was 75%.

EXAMPLE 6

Manufacturing of 3-(aminomethyl)-6-chloropyridine starting from 3-(isopropoxycarbonylaminomethyl)pyridine 1-oxide:

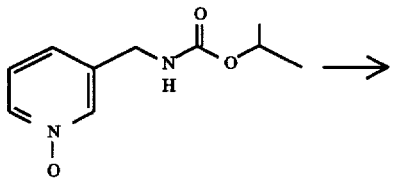

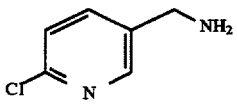

To 250 ml chloroform solution of 3-(isopropoxycarbonylaminomethyl) pyridine 1-oxide in an amount of 42.0 g (0.2 mol), was added trimethylamine in an amount of 29.6 g (0.5 mol), and the reaction mixture was then added phosgene in an amount of 24.0 g (0.24 mol) at −5° C. while stirring and spending 1 hour. The reaction mixture was then transferred into an autoclave whereto hydrogen chloride gas in an amount of 67.0 g (1.8 mol) was subsequently introduced, and the solution was allowed to a reaction for 5 hours at 50° C. under a pressure of 5 kgf/cm² while stirring. After cooling the reaction mixturen to a room temperature, the solution was then added with 35% hydrochloric acid in a volume of 160 ml to extract and separate the solution. The hydrochloric acid solution obtained was then heated for 3.5 hours at a temperature of from 90° to 95° C. After cooling it down to a room temperature, the reaction mixture was added with 28% aqueous solution of sodium hydroxide in a volume of 220 ml to adjust the pH of the solution to 13.5. The solution was then extracted with 150 ml chloroform and the aqueous layer was further repeatedly extracted with chloroform. All chloroform layers were collected together to dry it with magnesium sulfate and the solvent therein was then removed by distillation, thereby affording 3-(aminomethyl)-6-chloropyridine in an amount of 25.7 g (0.18 mol) in a crystalline form. The yield was 90%.

EXAMPLE 7

Manufacturing of 3-(aminomethyl)-6-chloropyridine starting from 3-(aminomethyl)pyridine:

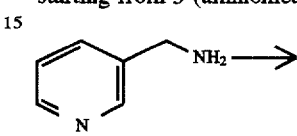

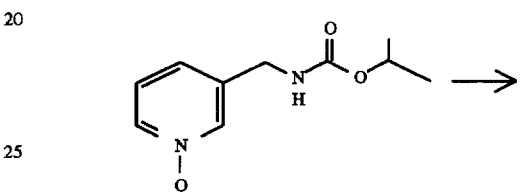

To a suspension consisting of 3-pyridine methane amine in an amount of 21.6 g (0.2 mol), 80 ml aqueous solution of sodium hydroxide in an amount of 8.8 g and chloroform in a volume of 60 ml, was fed dropwise isopropoxycarbonyl chloride in an amount of 25.7 g (0.21 mol) at a temperature of from 5° to 10° C. while stirring and spending 30 minutes, and the reaction mixture was further stirred for 30 minutes. After separating the mixture, the organic layer was concentrated under reduced pressure and was then dissolved in 20 ml water together with sodium tungstate in an amount of 0.58 g and 35% hydrochloric acid in an amount of 1.0 g. To this solution, 34.5% hydrogen peroxide solution in an amount of 27.6 g was fed dropwise at 100° C. while spending 30 minutes. After adjusting the pH of the solution to 5 and allowing the solution to proceed a reaction for 3.5 hours at 100° C., the solution was then cooled down to a room temperature and added with hypo to an extent that an iodo-starch reaction in the solution changes to the negative one. The reaction mixture was then repeatedly extracted with chloroform in a volume of 100 ml, and all of the chloroform solution collected together was subjected to an azeotropic dehydration. To 250 ml chloroform solution obtained as described above, was added trimethylamine in an amount of 30.0 g (0.51 mol), and the resultant solution was added phosgene in an amount of 24.0 g (0.24 mol) at −5° C. while stirring and spending 1 hour. The reaction mixture was then transferred into an autoclave, whereto hydrogen chloride gas in an amount of 67.0 g was subsequently introduced, and the solution was allowed to a reaction for 5 hours at 50° C. under a pressure of 5 kgf/cm² while stirring. After cooling the solution to a room temperature, the solution was then extracted with 35% hydrochloric acid in a volume of 160 ml. The aqueous solution of hydrochloric acid obtained was then heated for 3.5 hours at a temperature of from 90° to 65° C. After cooling the solution to a room temperature, the reaction mixture was then added with 28% aqueous solution of sodium hydroxide to adjust the pH of the solution to 13.5. The solution was then extracted with 150 ml chloroform, and the aqueous layer was further repeatedly extracted with chloroform. All chloroform layers were collected together to dry it with magnesium sulfate and the solvent therein was removed by distillation, thereby affording 3-(aminomethyl)-6-chloropyridine in an amount of 24.8 g in a crystalline form The yield was 87%.

Referential Example 1

Manufacturing of 3-(pivaloylaminomethyl)pyridine 1-oxide

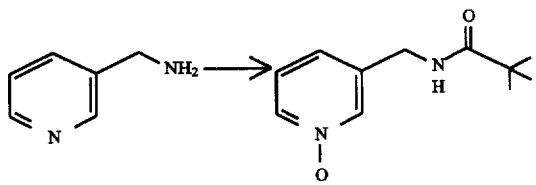

To a suspension consisting of 3-pyridine methane amine in an amount of 54.1 g (0.5 mol), sodium hydroxide in an amount of 30 g, water in a volume of 150 ml and chloroform in a volume of 500 ml, was fed dropwise pivaloyl chloride in an amount of 72.8 g (0.6 mol) at a temperature of from 5° to 10° C. while stirring and spending 30 minutes, and the reaction mixture was further stirred for 30 minutes. After separating the mixture, the organic layer was dried with magnesium sulfate, and the solvent therein was removed by distillation, thereby affording 3-(pivaloylaminomethyl)pyridine in an amount of 96.1 g (yield: 100%). The 3-(pivaloylaminomethyl)pyridine was then dissolved in water in a volume of 150 ml together with sodium tungstate in an amount of 1.65 g, and the reaction mixture was further fed dropwise with 34.5% aqueous solution of hydrogen peroxide in an amount of 70.0 g at 100° C. while stirring, adding 35% hydrochloric acid to adjust the pH of the solution to 5, and spending 50 minutes. The solution was further allowed to react for 4.5 hours and was added with hypo to an extent that an iodo-starch reaction in the solution changes to the negative one. The reaction mixture was concentrated and added chloroform, and then the chloroform solution was subjected to an azeotropic dehydration for completion of the solvent exchange. The chloroform solution was filtrated and concentrated under reduced pressure, thereby affording 3-(pivaloylaminomethyl)pyridine 1-oxide in an amount of 102.7 g. The yield was 98.6%.

$^1$H-NMR(CDCl$_3$); δ8.06(s, 1H), 8.05(s, 1H), 7.21(dd, J=3.6 and 3.6Hz, 2H), 6.79(brs, 1H), 4.39 (d, J=5.94 Hz, 2H), 1.24(s, 9H).

Referential Examples 2 through 12

According to the same procedure as described in the Referential Example 1, Referential Examples 2 through 12 were carried out and the results thereof were presented in Table 1 hereinbelow.

TABLE 1

Structural Formula

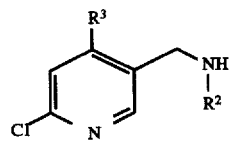

| Referential Examples Compound No. | R$^1$ | R$^2$ | R$^3$ | Yield (%) | Physical Data (Melting Point) |
|---|---|---|---|---|---|
| 2 | Ph | H | H | 86 | 112 ~ 113° C. |
| 3 | p-MeOC$_6$H$_4$ | H | H | 95 | 162 ~ 166° C. |
| 4 | p-MeC$_6$H$_4$ | H | H | 95 | 153 ~ 155° C. |
| 5 | p-ClC$_6$H$_4$ | H | H | 83 | 170 ~ 171° C. |
| 6 | o-MeC$_6$H$_4$ | H | H | 86 | 158 ~ 160° C. |
| 7 | o-ClC$_6$H$_4$ | H | H | 95 | 149 ~ 151° C.. |
| 8 | Ph | Me | H | 94 | *1) |
| 9 | OMe | H | H | 63 | 117 ~ 118° C. |
| 10 | OiPr | H | H | 96 | *2) |
| 11 | n-hexyl | H | H | 95 | 79 ~ 80° C. |
| 12 | heptadecyl | H | H | 96 | 87 ~ 91° C. |

*1) $^1$H-NMR(CDCl$_3$): δ 8.3–8.2 (m, 2H), 7.4–7.2 (m, 7H), 4.69 (brs, 2H), 2.98 (brs, 3H).
*2) $^1$H-NMR(CDCl$_3$): δ 8.18 (s, 1H), 8.11 (d, J=5.94, 1H), 7.36–7.22 (m, 2H), 6.92 (t, J=5.94, 1H), 5.02–4.82 (m, 1H), 4.32 (d, J=5.94, 2H), 1.20 (d, J=5.94, 6H).

Industrial Applicability

The manufacturing methods according to the present invention are excellent methods in an industrial scale in which no side reactions, such as dechlorination and dimer production, which are unavoidable in the past methods under the amination conditions, may occur by means of using a raw material having an amino group on the methyl group bonding at the 3rd-position of a pyridine ring.

What is claimed is:

1. Method for manufacturing 3-(aminomethyl)-6-chloropyridines represented by a general formula [II];

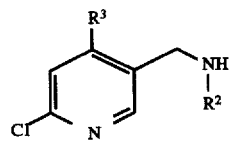

[II]

wherein R$^2$ represents hydrogen or a lower alkyl and R$^3$ represents hydrogen, a lower alkyl or an halogen atom, characterized in that the compound represented by the general formula [II] is manufactured by allowing 3-(substituted-aminomethyl)pyridine 1-oxide represented by a general formula [I];

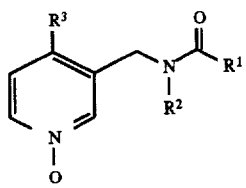

[I]

wherein R$^1$ represents alkyl, aryl, aralkyl or alkoxy, R$^2$ and R$^3$ are as described above, to react with a base represented by a general formula [a];

R'R"R'''N  [a]

wherein R', R" and R'" may be the same or different one another and represent each independently a lower alkyl or an aromatic group, or R', R", R'" and N may form together an optionally-substituted pyridine ring, in the presence of an electrophilic reagent having at least one chlorine atom, and subsequently treating the reaction product with hydrogen chloride and water.

2. The manufacturing method according to claim 1, wherein $R^3$ is hydrogen.

3. The manufacturing method according to claim 1, wherein $R^2$ is hydrogen.

4. The manufacturing method according to claim 1, wherein the base represented by a general formula [a] is trimethylamine, triethylamine, N, N-dimethylaniline or pyridine.

5. The manufacturing method according to claim 1, wherein the electrophilic reagent is any of phosgene, thionyl chloride, sulfuryl chloride, phosphorus oxychloride, phosphorus pentachloride, sulfonyl chlorides and chloroformates.

6. The manufacturing method according to claim 1, wherein the base represented by a general formula [a] is trimethylamine and the electrophilic reagent is phosgene.

7. The manufacturing method according to claim 1, wherein the reaction with a base represented by a general formula [a] is carried out in a nonaqueous solvent.

8. The manufacturing method according to claim 7, wherein the nonaqueous solvent is methylene chloride, chloroform, acetonitrile, THF, ethyl acetate, acetone or mixtures thereof.

9. The manufacturing method according to claim 1, wherein the treatment with hydrogen chloride is carried out in an aqueous solvent.

10. The manufacturing method according to claim 7, comprising a further hydrolysis step carried out in an aqueous solvent in the presence of an acid.

* * * * *

UNITED STATES PATENT AND TRADEMARK OFFICE
CERTIFICATE OF CORRECTION

PATENT NO. : 5,744,608
DATED      : April 28, 1998
INVENTOR(S) : Tsutomu Inoue, et al.

It is certified that error appears in the above-identified patent and that said Letters Patent is hereby corrected as shown below:

On the title page: Item [75]                           , the inventors' names should read as follows:

Tsutomu Inoue, Odawara; Jun Takahashi; Tsutomu Imagawa, both of Takaoka; Kazuhiro Hatanaka, Himi, all of Japan Signed and Sealed this Fifteenth Day of December, 1998

Attest:

BRUCE LEHMAN

*Attesting Officer*  *Commissioner of Patents and Trademarks*